United States Patent
Kwon

(10) Patent No.: US 7,932,045 B2
(45) Date of Patent: Apr. 26, 2011

(54) METHOD OF ISOLATING AND PROLIFERATING AUTOLOGOUS ANTIGEN-SPECIFIC CD8+ T CELL USING ANTI-4-1BB ANTIBODIES

(75) Inventor: Byoung Se Kwon, Ulsan (KR)

(73) Assignee: University of Ulsan Foundation for Industry Cooperation, Ulsan (KR)

( * ) Notice: Subject to any disclaimer, the term of this patent is extended or adjusted under 35 U.S.C. 154(b) by 337 days.

(21) Appl. No.: 12/010,048

(22) Filed: Jan. 18, 2008

(65) Prior Publication Data

US 2008/0261307 A1 Oct. 23, 2008

(30) Foreign Application Priority Data

Mar. 16, 2007 (KR) .................. 10-2007-0025814

(51) Int. Cl.
*G01N 33/53* (2006.01)
(52) U.S. Cl. .......................................... 435/7.1
(58) Field of Classification Search ............... None
See application file for complete search history.

(56) References Cited

U.S. PATENT DOCUMENTS

2004/0224402 A1* 11/2004 Bonyhadi et al. ............. 435/372
2009/0041763 A1* 2/2009 Kwon .......................... 424/133.1

FOREIGN PATENT DOCUMENTS

WO  WO2006/126835  * 11/2006

OTHER PUBLICATIONS

"Presentation of Interim Report on Industry, Academy and Research Institute Consortium for Technical Co-Development", Jan. 19, 2007, Foundation for Industry Cooperation, Ulsan University, 9 pages in Korean, 10 pages of English translation.
O'Neill, D.W., et al., "Manipulating Dendritic Cell Biology for the Active Immunotherapy of Cancer", Blood, Oct. 15, 2004, vol. 104, No. 8, pp. 2235-2246 (Abstract Only).
Preynat-Seauve, O., et al., "Tumor-infiltrating Dendritic Cells are Potent Antigen-Presenting Cells Able to Activate T Cells and Mediate Tumor Rejection", J. Immunol., vol. 176, No. 1, Jan. 1, 2006, pp. 61-67 (Abstract Only).
Zhang, X., et al., "CD4-8-dendritic Cells Prime CD4+ T Regulatory 1 Cells to Suppress Antitumor Immunity", J. Immunol., vol. 175, No. 5, Sep. 1, 2005, pp. 2931-2937 (Abstract Only).
Hurtado, J.C., et al., "Signals Through 4-1BB are Costimulatory to Previously Activated Splenic T Cells and Inhibit Activation-Induced Cell Death", J. Immunol., vol. 158, No. 6, Mar. 15, 1997, pp. 2600-2609 (Abstract Only).
Wilcox, R.A., et al., "Provision of Antigen and CD137 Signaling Breaks Immunological Ignorance, Promoting Regression of Poorly Immunogenic Tumors", J. Clin Invest., vol. 109, No. 5, Mar. 2002, pp. 651-659 (Abstract Only).
Kim, Y.H., et al., "4-1BB Costimulation Enhances HSV-1-Specific CD8+ T Cell Responses by the Induction of CD11c+CD8+ T Cells", Cell Immunol., vol. 238, No. 2, Dec. 2005, pp. 76-86 (Abstract Only).

* cited by examiner

*Primary Examiner* — Ilia Ouspenski
(74) *Attorney, Agent, or Firm* — Stites & Harbison PLLC; Juan Carlos A. Marquez, Esq.

(57) ABSTRACT

Provided are methods of isolating and proliferating antigen-specific CD8+ T cells using anti-4-1BB antibodies. The methods of isolating and proliferating CD8+ T cells may yield cells at a higher recovery rate than a conventional isolation method, and the isolation method using humanized anti-4-1BB antibodies may also yield cells at a high recovery rate. Further, in cell culture, cells may be grown at a high proliferation rate. The antigen-specific CD8+ T cells yielded according to the isolation and proliferation methods may be used to treat cancer without any side-effects.

13 Claims, 7 Drawing Sheets

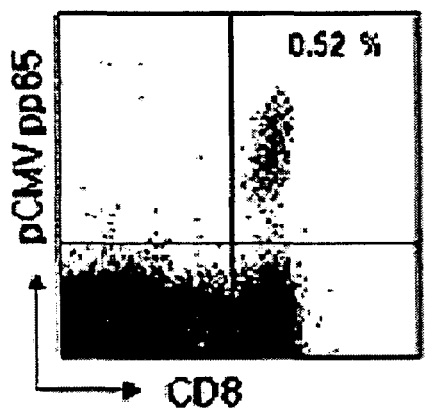
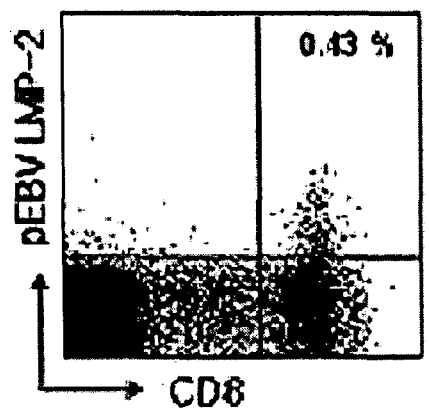

Fig. 2

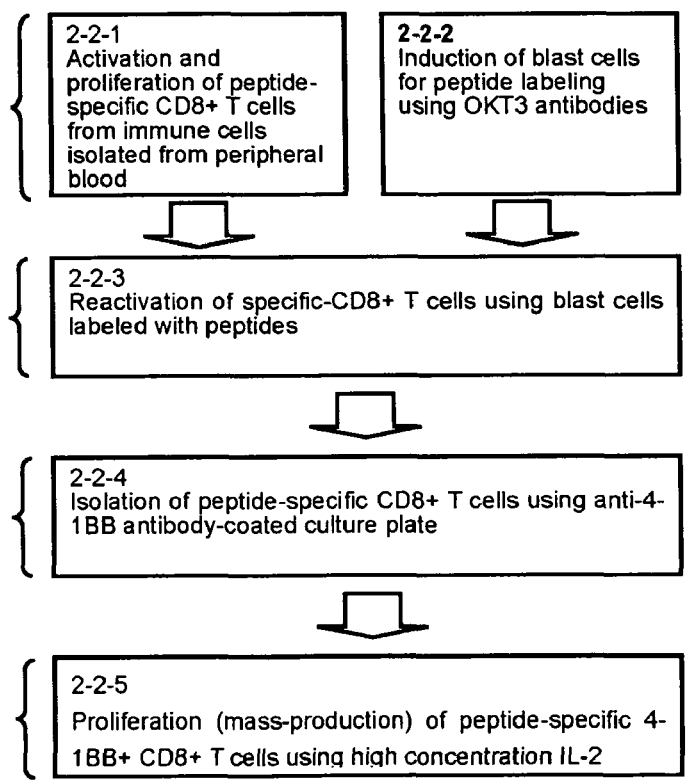

*Period of culture: 2 weeks
*Proliferation rate of peptide-specific CD8+ T cells: 25-100 times
*Population of pentamer+ CD8+ T cells: at least 30% at 4% or lower
*Increase in total number of cells: 0.5-3 times 2-2-1 Activation and proliferation of peptide-specific CD8+ T cells from immune cells isolated from peripheral blood 2-2-2 Induction of blast cells for peptide labeling using OKT3 antibodies

*Period of culture: 2 days
*Population of 4-1BB+ CD8+ T cells: at least 70%

2-2-3 Reactivation of specific-CD8+ T cells using blast cells labeled with peptides

*Period of culture: 2 hours
*Recovery rate of pentamer+CD8+ T cells: at least 60%

2-2-4 Isolation of peptide-specific CD8+ T cells using anti-4-1BB antibody-coated culture plate

*Period of culture: 2 weeks
*Proliferation rate of peptide-specific CD8+ T cells: 10-50 times
*Population of pentamer+ CD8+ T cells: at least 80%
*Increase in total number of cells: 10-50 times 2-2-5 Proliferation (mass-production) of peptide-specific 4-1BB+ CD8+ T cells using high concentration IL-2

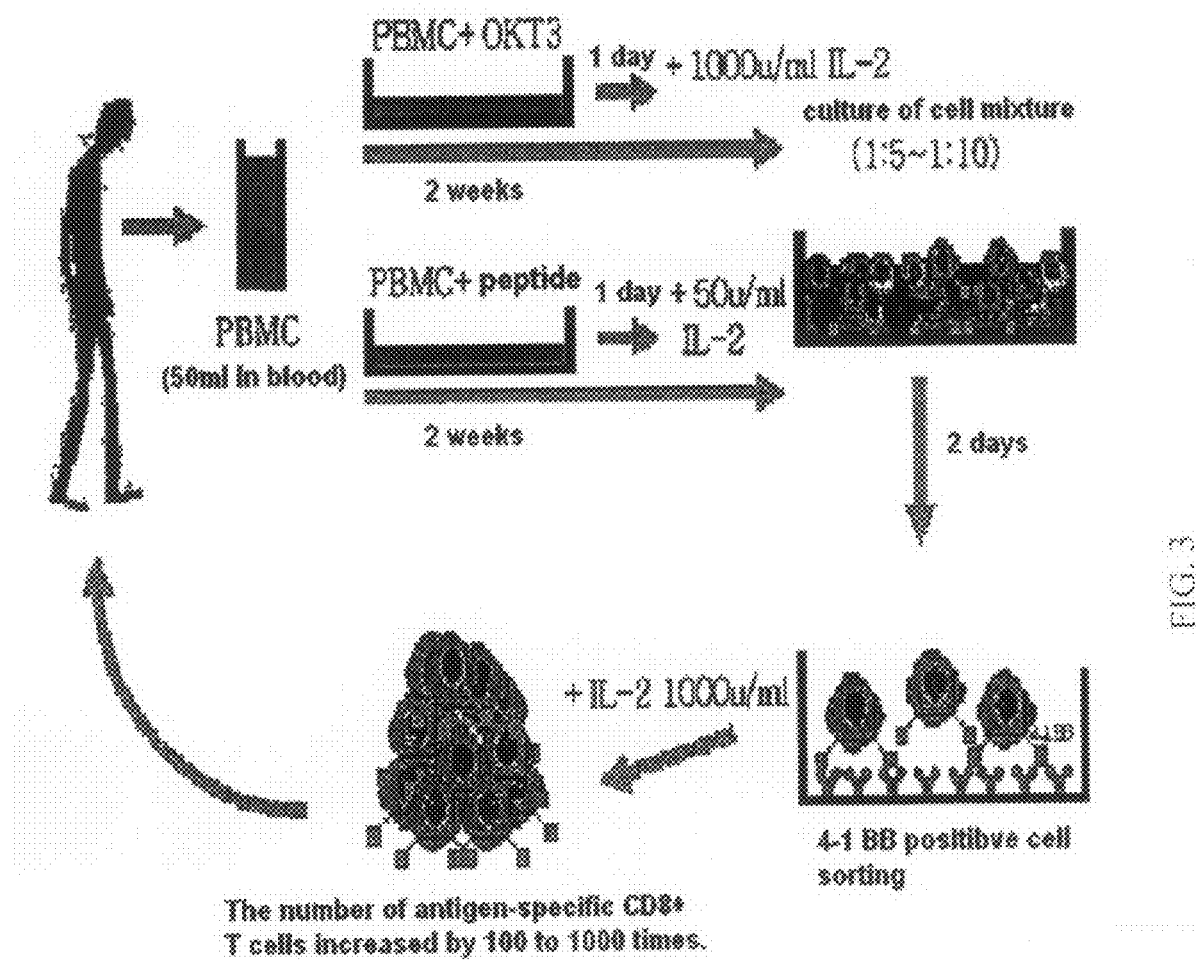

FIG. 5A
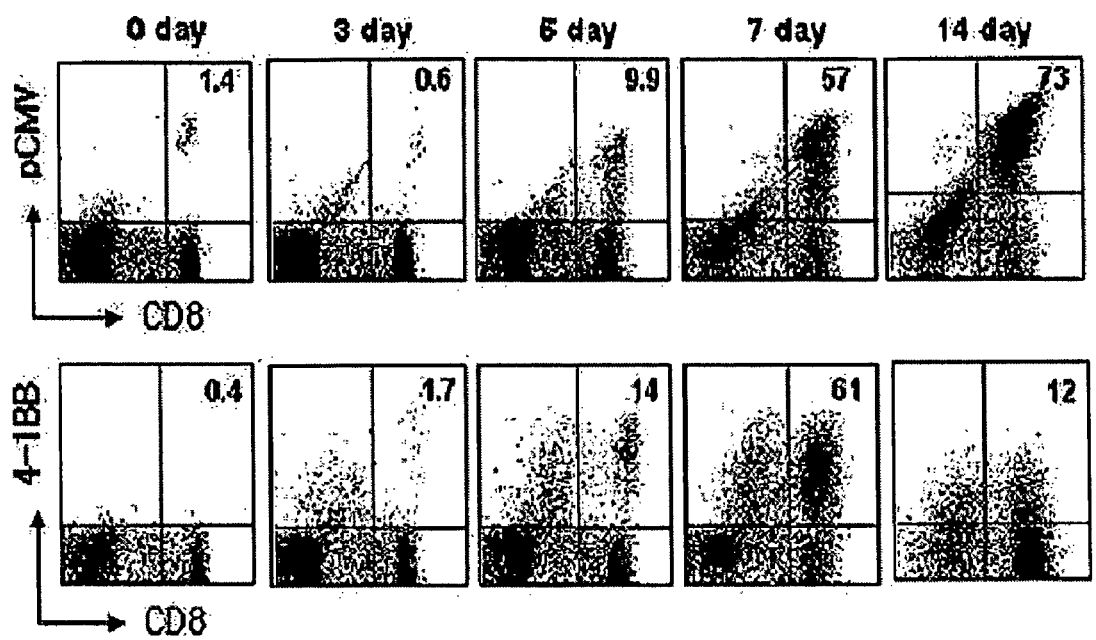
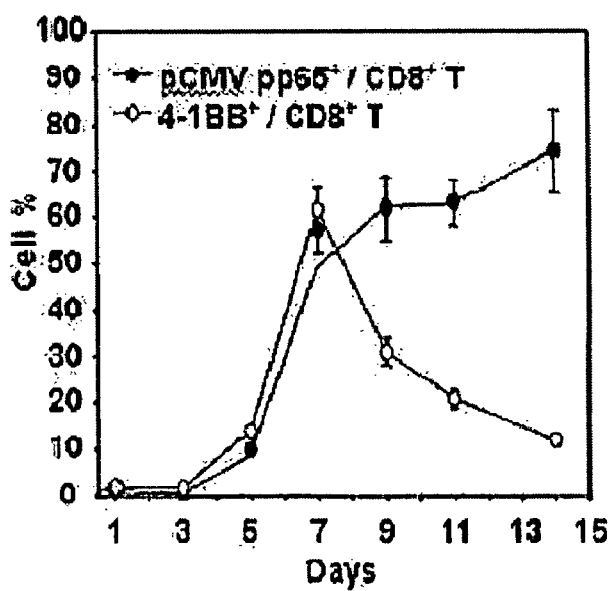
FIG. 5B

Fig. 8
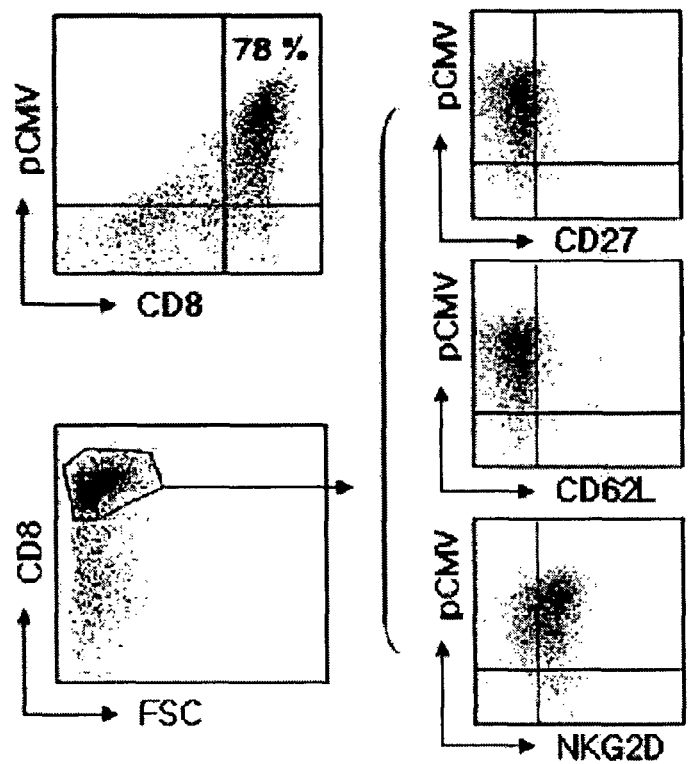
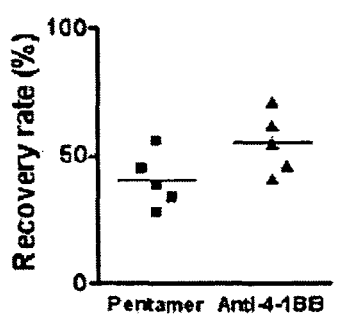
FIG. 9A
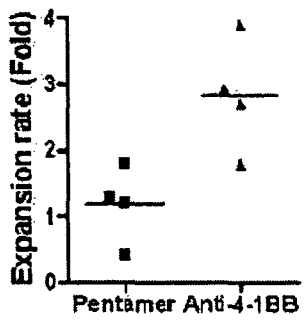
FIG. 9B
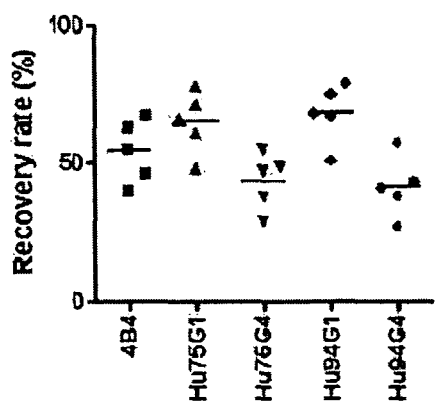
FIG. 9C

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Amino acid sequence of CMV pp65

<400> SEQUENCE: 1

Asn Leu Val Pro Met Val Ala Thr Val
 1               5

<210> SEQ ID NO 2
<211> LENGTH: 472
<212> TYPE: PRT
<213> ORGANISM: Artificial Sequence
<220> FEATURE:
<223> OTHER INFORMATION: Amino acid sequence of HBBK4-75G1 heavy chain

<400> SEQUENCE: 2

Asp Leu Thr Met Gly Trp Ser Cys Ile Ile Leu Phe Leu Val Ala Thr
 1               5                  10                  15

Ala Thr Gly Val His Ser Gln Val Gln Leu Gln Gln Ser Gly Ala Glu
                20                  25                  30

Val Ile Lys Pro Gly Ala Ser Val Lys Leu Ser Cys Lys Ala Ser Gly
            35                  40                  45

Tyr Thr Phe Ser Ser Tyr Trp Met His Trp Val Arg Gln Ala Pro Gly
        50                  55                  60

Gln Gly Leu Glu Trp Ile Gly Glu Ile Asn Pro Gly Asn Gly His Thr
65                  70                  75                  80

Asn Tyr Asn Glu Lys Phe Lys Ser Arg Ala Thr Leu Thr Gly Asp Thr
                85                  90                  95

Ser Thr Ser Thr Val Tyr Met Glu Leu Ser Ser Leu Arg Ser Glu Asp
            100                 105                 110
```

```
Thr Ala Val Tyr Tyr Cys Ala Arg Ser Phe Thr Thr Ala Arg Ala Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Lys Ser Leu
225                 230                 235                 240

Ser Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 3
<211> LENGTH: 465
<212> TYPE: PRT
<213> ORGANISM: Artificial Sequence
<220> FEATURE:
<223> OTHER INFORMATION: Amino acid sequence of HBBK4-75G4 heavy chain

<400> SEQUENCE: 3
```

-continued

```
Met Gly Trp Ser Cys Ile Ile Leu Phe Leu Val Ala Thr Ala Thr Gly
 1               5                  10                  15

Val His Ser Gln Val Gln Leu Gln Gln Ser Gly Ala Glu Val Ile Lys
             20                  25                  30

Pro Gly Ala Ser Val Lys Leu Ser Cys Lys Ala Ser Gly Tyr Thr Phe
             35                  40                  45

Ser Ser Tyr Trp Met His Trp Val Arg Gln Ala Pro Gly Gln Gly Leu
         50                  55                  60

Glu Trp Ile Gly Glu Ile Asn Pro Gly Asn Gly His Thr Asn Tyr Asn
 65                  70                  75                  80

Glu Lys Phe Lys Ser Arg Ala Thr Leu Thr Gly Asp Thr Ser Thr Ser
                 85                  90                  95

Thr Val Tyr Met Glu Leu Ser Ser Leu Arg Ser Glu Asp Thr Ala Val
             100                 105                 110

Tyr Tyr Cys Ala Arg Ser Phe Thr Thr Ala Arg Ala Phe Ala Tyr Trp
         115                 120                 125

Gly Gln Gly Thr Leu Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
             180                 185                 190

Ala Val Leu Gln Ser Ser Gly Leu Tyr Ser Leu Ser Ser Val Val Thr
             195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
             260                 265                 270

Arg Thr Pro Glu Val Thr Cys Val Val Val Asp Val Ser Gln Glu Asp
             275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
             340                 345                 350

Thr Ile Ser Lys Ala Lys Gly Gln Pro Arg Glu Pro Gln Val Tyr Thr
             355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
             420                 425                 430
```

-continued

```
Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
        450                 455                 460

Lys
465

<210> SEQ ID NO 4
<211> LENGTH: 236
<212> TYPE: PRT
<213> ORGANISM: Artificial Sequence
<220> FEATURE:
<223> OTHER INFORMATION: Amino acid sequence of HBBK4-75G1 and 75G4
      Light chain

<400> SEQUENCE: 4

Leu Asp Met Met Arg Phe Ser Ala Gln Phe Leu Gly Leu Leu Leu Leu
1               5                   10                  15

Cys Phe Gln Gly Thr Arg Cys Asp Ile Val Met Thr Gln Ser Pro Ala
            20                  25                  30

Phe Leu Ser Val Thr Pro Gly Glu Lys Val Thr Ile Thr Cys Arg Ala
        35                  40                  45

Ser Gln Thr Ile Ser Asp Tyr Leu His Trp Tyr Gln Gln Lys Pro Asp
    50                  55                  60

Gln Ala Pro Lys Leu Leu Ile Lys Tyr Ala Ser Gln Ser Ile Ser Gly
65                  70                  75                  80

Ile Pro Ser Arg Phe Ser Gly Ser Gly Ser Gly Thr Asp Phe Thr Phe
                85                  90                  95

Thr Ile Ser Ser Leu Glu Ala Glu Asp Ala Ala Thr Tyr Tyr Cys Gln
            100                 105                 110

Asp Gly His Ser Phe Pro Pro Thr Phe Gly Gln Gly Thr Lys Leu Glu
        115                 120                 125

Ile Lys Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 5
<211> LENGTH: 472
<212> TYPE: PRT
<213> ORGANISM: Artificial Sequence
<220> FEATURE:
<223> OTHER INFORMATION: Amino acid sequence of HBBK4-94G1 heavy chain

<400> SEQUENCE: 5

Asp Leu Thr Met Gly Trp Ser Cys Ile Ile Leu Phe Leu Val Ala Thr
1               5                   10                  15

Ala Thr Gly Val His Ser Gln Val Gln Leu Gln Gln Ser Gly Ala Glu
```

```
                    20                  25                  30
Val Lys Lys Pro Gly Ala Ser Val Lys Leu Ser Cys Lys Ala Ser Gly
                35                  40                  45
Tyr Thr Phe Ser Ser Tyr Trp Met His Trp Val Arg Gln Ala Pro Gly
            50                  55                  60
Gln Gly Leu Glu Trp Ile Gly Glu Ile Asn Pro Gly Asn Gly His Thr
 65                  70                  75                  80
Asn Tyr Asn Glu Lys Phe Lys Ser Arg Ala Thr Met Thr Arg Asp Thr
                85                  90                  95
Ser Thr Ser Thr Ala Tyr Met Glu Leu Ser Ser Leu Arg Ser Glu Asp
                100                 105                 110
Ser Ala Val Tyr Tyr Cys Ala Arg Ser Phe Thr Ala Arg Ala Phe
                115                 120                 125
Ala Tyr Trp Gly Gln Gly Thr Leu Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
        210                 215                 220
Asn Val Asn His Lys Pro Ser Asn Thr Lys Val Asp Lys Lys Ser Leu
225                 230                 235                 240
Ser Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
        290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Glu Glu Met Thr
        370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
```

```
Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 6
<211> LENGTH: 465
<212> TYPE: PRT
<213> ORGANISM: Artificial Sequence
<220> FEATURE:
<223> OTHER INFORMATION: Amino acid sequence of HBBK4-94G4 Heavy chain

<400> SEQUENCE: 6

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Leu Ser Cys Lys Ala Ser Gly Tyr Thr Phe
        35                  40                  45

Ser Ser Tyr Trp Met His Trp Val Arg Gln Ala Pro Gly Gln Gly Leu
    50                  55                  60

Glu Trp Ile Gly Glu Ile Asn Pro Gly Asn Gly His Thr Asn Tyr Asn
65                  70                  75                  80

Glu Lys Phe Lys Ser Arg Ala Thr Met Thr Arg Asp Thr Ser Thr Ser
                85                  90                  95

Thr Ala Tyr Met Glu Leu Ser Ser Leu Arg Ser Glu Asp Ser Ala Val
            100                 105                 110

Tyr Tyr Cys Ala Arg Ser Phe Thr Thr Ala Arg Ala Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335
```

```
Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Gln Glu Glu Met Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
            450                 455                 460

Lys
465

<210> SEQ ID NO 7
<211> LENGTH: 236
<212> TYPE: PRT
<213> ORGANISM: Artificial Sequence
<220> FEATURE:
<223> OTHER INFORMATION: Amino acid sequence of HBBK4-94G1 and 94G4
      light chain

<400> SEQUENCE: 7

Leu Asp Met Met Arg Phe Ser Ala Gln Phe Leu Gly Leu Leu Leu Leu
 1               5                  10                  15

Cys Phe Gln Gly Thr Arg Cys Asp Val Val Met Thr Gln Ser Pro Ala
            20                  25                  30

Phe Leu Ser Val Thr Pro Gly Glu Lys Val Thr Ile Thr Cys Arg Ala
            35                  40                  45

Ser Gln Thr Ile Ser Asp Tyr Leu His Trp Tyr Gln Gln Lys Pro Asp
        50                  55                  60

Gln Ala Pro Lys Leu Leu Ile Lys Tyr Ala Ser Gln Ser Ile Ser Gly
65                  70                  75                  80

Ile Pro Ser Arg Phe Ser Gly Ser Gly Ser Gly Thr Asp Phe Thr Phe
                85                  90                  95

Ser Ile Ser Ser Val Glu Ala Glu Asp Val Gly Ala Tyr Tyr Cys Gln
            100                 105                 110

Asp Gly His Ser Phe Pro Pro Thr Phe Gly Gln Gly Thr Lys Leu Glu
            115                 120                 125

Ile Lys Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205
```

-continued

```
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

METHOD OF ISOLATING AND PROLIFERATING AUTOLOGOUS ANTIGEN-SPECIFIC CD8+ T CELL USING ANTI-4-1BB ANTIBODIES

BACKGROUND OF THE INVENTION

1. Field of the Invention

The present invention relates to a method of isolating and proliferating autologous, antigen-specific CD8+ T cells using anti-4-1BB antibodies.

2. Description of the Related Art

Research into the treatment of cancer using a patient's autoimmune system has been going on for a long time. The main targets of such treatment are dendritic cells (DCs) and CD8+ T cells (O'Neill D W et al., Manipulating dendritic cell biology for the active immunotherapy of cancer, Blood, 104, pp. 2235-2246, 2004). The DCs are potent antigen-presenting cells that are able to induce strong immunity to a labeled antigen, and thus have been studied as promising immunotherapeutics candidates (Preynat-Seauve O et al., Tumor-infiltrating dendritic cells are potent antigen-presenting cells able to activate T cells and mediate tumor rejection, J Immunol., 176, pp. 61-67, 2006). However, recent reports indicate that functional diversity of the DC brings about suppression of immunity as well as enhancement of immunity that has been expected to occur in a living body (Zhang X et al., CD4-8-dendritic cells prime CD4+ T regulatory 1 cells to suppress antitumor immunity, J immunol, 175, pp. 2931-2937, 2005). It is expected that cancer treatment using DCs is also directed to strong activation of CD8+ T cells, and CD8+ T cell-induced antitumor immunity may suppress a recurrence of the tumor cell by producing a memory T cell.

The CD8+ T cells have less probability to exhibit unexpected side-effects since they have a relatively simpler function than other cells, for example, DCs, CD4+ T cells and NK cells. The present inventor has been conducting a study of 4-1BB (CD137), an immunoregulatory protein, for a long period of time, and has come a long way in analyzing its characteristics and immunoregulation. The in vitro and in vivo characteristics of a 4-1BB stimulus are as follows. From results of the long in-vitro experiment on CD4+ and CD8+ T cells, it can be noted that CD8+ T cells stimulated by 4-1BB exhibit strong cytotoxicity, high expression of IFN-γ, and inhibition of activation-induced cell death (AICD) (Hurtado J C et al., Signals through 4-1BB are costimulatory to previously activated splenic T cells and inhibit activation-induced cell death, J Immunol., 158, pp. 2600-2609, 1997). Based on such characteristics of the 4-1 BB stimulus, which are appropriate for cancer treatment, a therapeutic effect on cancer using anti-4-1BB mAb was proven through an animal model (Wilcox R A et al., Provision of antigen and CD137 signaling breaks immunological ignorance, promoting repression of poorly immunogenic tumors, J Clin Invest., 109, pp. 651-659, 2002).

In response to effects of a cellular 4-1BB chain reaction, a chain reaction of the CD4+ T cell exhibits inductive expression by TCR activation, enhanced proliferation, cell cycle progression, AICD inhibition, production of Th1 cytokines such as IL-2, IFN-γ and IL-4, and increased memory formation. Further, a chain reaction of the CD8+ T cell exhibits inductive expression by TCR activation, enhanced proliferation, AICD inhibition, production of Th1 cytokines such as IL-2, IFN-γ and TNF-α, enhanced cytotoxic function, and increased memory formation.

In response to effects of an in vivo 4-1BB chain reaction, a cancer model exhibits an increased lifespan of a tumor-bearing mouse and cancer growth inhibition by enhanced CD8+ T reaction, an autoimmune disease model exhibits inhibition of disease progression by suppression of an antigen-specific CD4+ T cell, a viral infection model exhibits virus propagation inhibition by enhanced CD4+ T cell reaction, Listeria infection model exhibits protection of a Listeria-infected mouse, a GVHD model exhibits GVHD prevention by inhibition of CD4+ T cell reaction, and a transplantation model exhibits promotion of transplant rejection.

4-1BB, an inductive costimulatory molecule, is expressed in an activated CD8+ T cell. Thus, when CD8+ T cell is stimulated by a peptide, 4-1BB is generally expressed in the CD8+ T cell specifically activated by the peptide, and thus the cells may be isolated. By such a principle, only an activated and peptide-specific CD8+ T cell is isolated from peripheral blood mononuclear cells (PBMCs) which have been isolated from a patient's blood. The isolated CD8+ T cell is to be injected back into the patient after being proliferated as much as necessary using IL-2. An MHC-class I pentamer is an agent distinguishing an antigen-specific CD8+ T cell by forming a complex with a peptide to specifically bind to TCR.

Most people have been infected by CMV during their growth, and thus have immunological memories against CMV in a T cell, which has strong antigenicity, thereby inducing proliferation of antigen-specific CD8+ T cells. Accordingly, MHC class I pentamers for detecting such CMV-specific CD8+ T cells have been also developed, and are now commercially available.

Most people have been infected by Epstein-Barr virus (EBV), the most common virus, in childhood, but generally exhibit no symptoms. However, they still have immunological memories. The EBV also relates to various types of human malignant tumors, which is a main cause of African Burkitt lymphoma (BL) and nasopharyngeal carcinoma (NPC). In addition, EBV is reportedly linked to many diseases related to T cell dysfunction due to AIDS and immune suppressive drugs after transplantation, hairy leukoplakias, B cell lymphoproliferative diseases (EBV-LPDs), Hodgkin's lymphomas, gastric carcinomas, some breast carcinomas, etc. Since many people have memory T cells against the EBV, which is a viral antigen, the EBV can induce a stronger immune response than common antigens. Due to its high reactivity of CD8+ T cells and many patients, the EBV serves as a good test model for development of CTL cell therapy products using peptides and anti-4-1 BB antibodies.

After attempts to establish a therapeutic method of producing CD8+ T cell therapy products which are essential for eliminating tumor cells and specifically response to cytomegarovirus (CMV) pp65, the present invention was completed by providing methods of massively isolating and proliferating CD8+ T cells specifically responding to CMV pp65 and confirming that the CD8+ T cells yielded by these methods can be used to treat cancer without any side effects.

SUMMARY OF THE INVENTION

An embodiment of the invention provides methods of isolating and proliferating antigen-specific CD8+ T cells, which exhibit a high recovery rate in isolation and a high proliferation rate in cell culture after isolation, using humanized anti-4-1BB antibodies.

Thus, the invention is directed to providing a method of isolating antigen-specific CD8+ T cells using anti-4-1 BB antibodies.

The invention is also directed to providing a method of proliferating antigen-specific CD8+ T cells isolated by the above method.

In one aspect, the present invention provides a method of isolating antigen-specific CD8+ T cells using anti-4-1BB antibodies, which includes the steps of: (1) isolating PMBCs from a blood sample and culturing the cells in media containing CMV peptides and IL-2; (2) isolating PMBCs from the same blood sample as step (1), culturing the cells in media containing OKT3 and IL-2, and washing and labeling the cells with peptides; (3) culturing a cell mixture consisting of the cells in step (1) and the cells in step (2) in a range of ratios of 1:1 up to 1:20, preferably 1:5 to 1:10 for 1 to 5 days, preferably 1 or 2 days for reactivation; (4) culturing the mixture in step (3) in an anti-4-1BB mAb coated culture plate and removing unattached or non-specifically bound cells; and (5) culturing attached cells in step (4) and harvesting the cultured cells.

In step (1), the media may contain IL-2 and autologous plasma or autologous serum, and the cells may be cultured for 7 to 21 days, preferably, 12 to 16 days, and more preferably, 14 days.

In step (2), conditions of media and culture time may be the same as in step (1), and the peptides may be CMV pp65-derived peptides.

In step (3), the cells may be cultured in X-VIVO media containing IL-2 and autologous plasma or autologous serum.

In step (4), the cells may be cultured for 1 to 5 hours, preferably, 1 to 3 hours, and more preferably, 30 minutes to 1 hour.

In step (5), the cells may be cultured in X-VIVO media containing IL-2 and autologous plasma or autologous serum, for 7 to 21 days, preferably 10 to 18 days, and more preferably 10 to 14 days.

In another aspect, the present invention provides a method of isolating antigen-specific CD8+ T cells using humanized anti-4-1BB antibodies.

The humanized anti-4-1BB antibodies may be antibodies selected from SEQ. ID. Nos. 2, 3, 5 and 6. More particularly, HBBK4-75G1 of SEQ. ID. No. 2 and HBBK4-75G4 of SEQ. ID. No. 3 may indicate amino acid sequences in heavy chains of these antibodies, which have the same light chain represented by SEQ. ID. No. 4. Further, HBBK4-94G1 of SEQ. ID. No. 5 and HBBK4-94G4 of SEQ. ID. No. 6 may indicate amino acid sequences in heavy chains of these antibodies, which have the same light chain represented by SEQ. ID. No. 7. The HBBK4-75G1 antibody used herein has a heavy chain represented by SEQ. ID. No. 2 and a light chain represented by SEQ. ID. No. 4, the HBBK4-75G4 antibody used herein has a heavy chain represented by SEQ. ID. No. 3 and a light chain represented by SEQ. ID. No. 4, the HBBK4-94G1 antibody used herein has a heavy chain represented by SEQ. ID. No. 5 and a light chain represented by SEQ. ID. No. 7, and the HBBK4-94G4 antibody used herein has a heavy chain represented by SEQ. ID. No. 6 and a light chain represented by SEQ. ID. No. 7.

In still another aspect, the present invention provides a method of proliferating antigen-specific CD8+ T cells isolated by the above isolation method.

To be specific, the present invention may provide a method of proliferating antigen-specific CD8+ T cells by culturing antigen-specific CD8+ T cells isolated by either of the above isolation methods in media containing autologous plasma and IL-2.

The cells may be cultured for 1 to 20 days, preferably 10 to 18 days, and more preferably 12 to 16 days.

The antigen-specific CD8+ T cells isolated and proliferated by the present invention may be derived from and then directly applied to the same patient as cell therapy products.

The method of isolating antigen-specific CD8+ T cells can isolate cells at a high recovery rate, and the isolated cells may be grown at a high proliferation rate in comparison with a conventional method of isolating antigen-specific CD8+ T cells using tetramers or pentamers. While the conventional method may exhibit a very low recovery rate due to low affinity of tetramers or pentamers, the present isolation method overcomes an affinity issue, as is proven by expression of 4-1BB in an activated CD8+ T cell at a constant level, and exhibits a high recovery rate in isolation of the cells using humanized anti-4-1BB antibodies.

BRIEF DESCRIPTION OF THE DRAWINGS

The above and other objects, features and advantages of the present invention will become apparent by describing certain exemplary embodiments thereof with reference to the attached drawings in which:

FIG. 1A illustrates population of CMV-specific CD8+ T cells and FIG. 1B illustrates population of EBV-specific CD8+ T cells;

FIG. 2 illustrates a production protocol for isolation and proliferation methods according to the present invention;

FIG. 3 is an outline illustrating a development process of cell therapy products using EBV-specific CD8+ T cells;

FIG. 5A illustrates the distributions of pCMV pp65+ and 4-1BB+ CD8+ T cell populations by a peptide stimulus. FIG. 5B illustrates the population growth of pCMV pp65+ and 4-1BB+ CD8+ T cells;

FIG. 8 illustrates phenotypes of isolated pCMV+ CD8+ T cells;

FIG. 9A illustrates the recovery rate relating to the isolation of antigen-specific CD8+ T cells using anti-4-1BB antibodies. FIG. 9B shows the proliferation rate estimated for the isolation of the CD8+ T cells. FIG. 9C shows the recovery rates of the antigen-specific CD8+ T cells isolated using humanized anti-41BB antibodies;

DETAILED DESCRIPTION OF THE INVENTION

Figure 4:
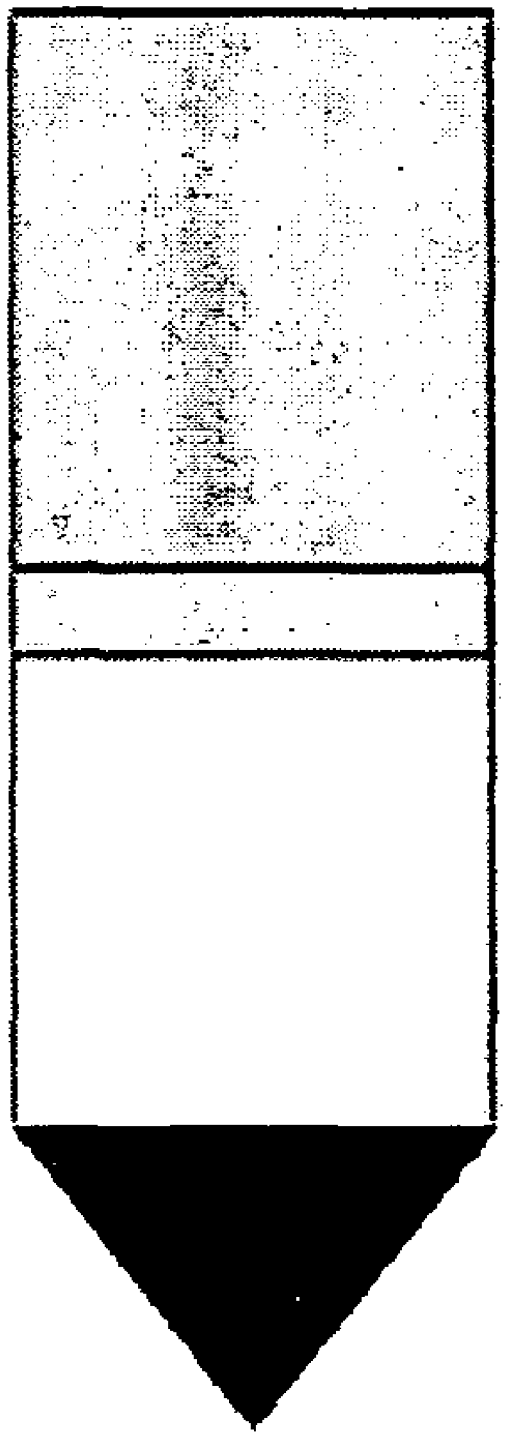
FIG. 4 illustrates isolation of PBMCs using ficoll by a density gradient.

The present invention will now be described more fully hereinafter with reference to the accompanying exemplary embodiments and experimental examples. This invention may, however, be embodied in different forms and should not be construed as limited to the embodiments and examples set forth herein.

1. Materials

Anti-CD8-FITC, anti-CD8-PE-Cy5, anti-4-1BB-PE, anti-CDllc-PE-Cy5, anti-CD57-FITC, anti-NKG2D-FITC, anti-CD62L-FITC, anti-CD27-FITC, anti-CD107a (LAMP-1)-biotin and streptavidin-PE used herein were purchased from eBioscience (San Diego, Calif.). EBV (LMP-2 CLG-GLLTMV)- and CMV (pp65 NLVPMVATA)-specific peptides were customized from Peptron (Dae-jeon, Korea).

X-VIVO media available for a cGMP grade was purchased from BioWhittacker (Wakersville, Md.). IM HEPES, RPMI1640, L-glutamine, 2-mercaptoethanol and penicillin/streptomycin (×100) were purchased from Invitrogen (San Diego, Calif.). CMV pp65 and EBV LMP-2 pentamers used to detect CMV- and EBV-specific CD8+ T cells were purchased from Proimmune (Oxford, U.K.). Anti-PE-microbeads were purchased from Miltenyi Biotec (Auburn, Calif.). Anti-4-1BB (4B4) and humanized anti-4-1BB mAb (Hu75G1, Hu75G4, Hu94G1 and Hu94G4) were designed and produced at the Immunomodulation Research Center (IRC) at Ulsan University. All blood samples used herein were donated by healthy volunteers and used in accordance with the guidelines of the institutional review board of the IRC at Ulsan University.

2. Selection of Volunteers having CMV Pentamer+ CD8+ T Cells in Peripheral Blood 5 ml blood samples were taken from approximately 20 volunteers, and diluted with the same volume of PBS. The diluted blood was pipetted into a separate 15 ml tube, and 3 ml of ficoll (Pharmacia) was slowly pipetted into the tube to set up a density gradient. The tube was centrifuged at 2000 rpm for 20 minutes to isolate PBMCs. The isolated cells were washed twice with PBS, and 10 µl of human IgG (1 mg/ml) was added to prevent non-specific binding. Without washing the cells, anti-CD8-FITC and pCMV pp65 or EBV LMP-2 pentamer were added and then kept for 30 minutes to stain the cells. After washing the stained cells with PBS, populations of CMV pp65-specific CD8+ T cells and EBV LMP-2-specific CD8+ T cells were measured on a flow cytometer, and the results are illustrated in FIG. 1. Particularly, it can be understood that CMV pp65-specific CD8+ T cells are activated and proliferated due to CMV peptides illustrated in FIG. 1A, and when cells have to be isolated using tetramers or pentamers, which have low affinity, in the presence of EBV illustrated in FIG. 1B, a cell recovery rate decreases.

Experimental Example 1

Isolation and Proliferation of Antigen-Specific CD8+ T Cells

To produce CTL cell therapy products for cancer, PBMCs were isolated from 50 ml of peripheral blood from a patient, and CMV pp65 peptides were added thereto. The cell mixture was cultured for 14 days in autologous plasma or autologous serum-contained media to induce proliferation of CMV peptide+ CD8+ T cells (group 1). At the same time, blast T cells were prepared by activation and proliferation of PBMCs, which were induced by OKT3 for 14 days in the same manner as group 1 (group 2). Among the two different groups of cells cultured for 14 days, the cells in group 2 were labeled with peptides for reactivation of the cells in group 1. The cells in groups 1 and 2 were mixed in ratios of 1:1 up to 1:10 to induce expression of 4-1BB, and cultured for two days. Then, the cells were plated on an anti-4-1BB mAb-coated culture plate and cultured for an hour to harvest only 4-1BB+ cells. The harvested cells were cultured in X-VIVO media containing 1000 U/ml of IL-2 for two weeks for proliferation, and by a cytotoxicity test, the function of the cells was proven to determine whether or not to administer the cells to the patient. An outline of the above procedure and checklists for individual steps in a process of producing cell therapy products are illustrated in FIGS. 2 and 3.

1-1. Induction and Differentiation of CMV Peptide-Specific CTLs

1) Peripheral blood samples (50 ml) were taken from an HLA-A2-positive patient using heparin (Using EDTA or citric acid is not permitted).
2) A mixture consisting of equal amounts of the blood and RPMI1640 media was pipetted into four 50 ml conical tubes by 25 ml, and 10 ml of ficoll (density: 1.077) was added into the bottom of each tube containing the mixture to set up a density gradient. The tubes were centrifuged at 900×g for 20 minutes. RPMI 1640 (Invitrogen, Cat# 11875-093)
3) After centrifugation, a PBMC layer was formed as illustrated in FIG. 4, autologous plasma and PBMCs were sequentially pipetted off from the tube using a disposable 10 ml pipette, and the autologous plasma was kept at 4° C. until needed.
4) The PBMCs were transferred to a new 50 ml conical tube, and fresh RPMI1640 medium was fully added to the tube. The tube was centrifuged into a pellet at 1200 rpm for 5 minutes, and then the pellet was washed. The pellet was again centrifuged and washed.
5) The cells were suspended in RPMI1640 media containing 5% autologous plasma, and then counted to have a concentration of 1×106 cells/ml.
6) CMV pp65 peptides were added to a ¾ volume of the PBMC suspension at a concentration of 0.5-1 µg/ml.
   CMV pp65 (SEQ. ID. No. 1: 495-504 amino acids, NLVPMVATV); HLA-A*0201-restricted
7) The peptide-added PMBC suspension was pipetted into a T-75 culture flask at 1×107 cells/10 ml/flask.
   T-75 culture flask (Nunc, Cat# 156499)
8) The cells contained in the flask were cultured in a 5% CO2-humidified incubator at 37° C.
9) On the 2nd day of the cell culture (PI day 2), 10 ml of RPMI1640 media containing 5% autologous plasma and 50 IU/ml of human IL-2 was added to the flask.
10) On the 7th day of the cell culture (PI day 7), 10 ml of cell culture media was removed, and then 10 ml of fresh RPMI1640 media containing 5% autologous plasma and 50 IU/ml of human IL-2 was added.
11) 10 ml of culture media was removed, and the 10 ml of fresh RPMI 1640 media containing 5% autologous plasma and 50 IU/ml of human IL-2 was added every second day (PI day 9, 11 and 13).
12) On the 14th day of the cell culture, formation of EBV- or CMV-specific CTLs was confirmed using an MHC pentamer.
   SEQ. ID. No. 1 (CMV pp65 NLVPMVATV, Proimmune, HLA-A*0201)

As described above, 50 ml blood samples were taken from a pCMV pp65 (CMV pp65 pentamer)-positive volunteer, and PBMCs were isolated from the blood sample. The PBMCs were cultured with CMV pp65 NLVPMVATV peptides in a T-75 flask for 14 days, and some of the PBMCs were taken to compare populations of pCMV pp65+ CD8+ T cells and 4-1BB+ CD8+ T cells. In result, as illustrated in FIG. 5A, the population of the pCMV+ CD8+ T cells gradually increases as time passes, and so does the population of the 4-1BB+ CD8+ T cells. However, the population of the 4-1BB+ CD8+ T cells reaches the uppermost level approximately between the 7th and 9th days, and then gradually decreases. FIG. 5B is a graph illustrating the populations of pCMV pp65+ CD8+ T cells and 4-1BB+ CD8+ T cells.

From these results, it can be confirmed that CMV pp65-specific CD8+ T cells are activated and proliferated due to CMV peptides, and an increase in 4-1BB expression goes with the increased number of antigen-specific CD8+ T cells.

1-2. Production of Blast T Cells for Peptide Labeling

1) A ¼ volume of the PBMCs recovered in experimental example 1-1-4) was used to produce blast T cells for peptide labeling.
2) RPMI1640 media was added to fill a 50 ml conical tube containing the PBMCs. The tube was centrifuged into a pellet at 1200 rpm for 5 minutes, and the pellet was washed. The pellet was again centrifuged and washed.
3) The cells were suspended in X-VIVO 10 media, and then counted to have a concentration of 1×106 cells/ml.
   X-VIVO 10 medium (Cambrex BioWhittaker, cGMP grade)
4) OKT3 antibodies were added to the PBMC suspension at a concentration of 1 μg/ml, and then the mixture was transferred to a T-75 culture flask at 1×107 cells/10 ml/flask.
5) The cells were cultured in a 5% CO2-humidified incubator at 37° C.
6) On the 1st day of the cell culture (PI day 1), 10 ml of X-VIVO 10 media containing 1000 IU/ml human IL-2 was added to the flask.
7) 10 ml of the cell culture media was exchanged with the same amount of fresh X-VIVO 10 media containing 100 IU/ml human IL-2 every second day until the 14th day of the cell culture (PI day 14).
8) Whenever the media turned yellow (approximately every second day), 10 ml of the culture media was removed, and then 10 ml of fresh X-VIVO 10 media containing 1000 IU/ml human IL-2 was added.
9) On the 14th day of the cell culture (PI day 14), entire cells in the flask were harvested and transferred to a new 50 ml conical tube. The tube was filled to the top with X-VIVO 10 media, a centrifuged into a pellet at 1200 rpm for 5 minutes, and then the pellet was washed. The pellet was again centrifuged and washed.
10) The cells were suspended in protein-free X-VIVO 10 media at a concentration of 1×106 cells/ml, and then 1 g/ml of EBV LMP-2 or CMV peptides were added to the cells for labeling.
11) The cells were kept at room temperature for 30 minutes until labeled.
12) The tube having the cells was filled to the top with X-VIVO 10 media, centrifuged into a pellet at 1200 rpm for 5 minutes, and then the pellet was washed. Again, the pellet was centrifuged and washed twice, thereby preparing CMV peptide-pulsed OKT3-T cells.

1-3. Reactivation of Peptide-Specific CD8+ T Cells

From the results of experimental example 1-1, it can be proven that CMV pp65-specific CD8+ T cells increase in number when PBMCs are cultured with CMV peptides. However, between the 7th and 9th days of the cell culture, expression of 4-1BB reaches its maximum and then goes down. Accordingly, antigen-specific CD8+ T cells need to be reactivated, and for this reason, blast T cells were used herein to maximize the reactivation. The blast T cells were prepared by the method described in experimental example 1-2.

1) The peptide-specific CTLs prepared according to experimental example 1-1 were mixed with the peptide-pulsed OKT3-T cells prepared according to experimental example 1-2 in a range of ratios from 1:1 to 10:1, and then the mixture was cultured in a T-75 culture flask. Herein, RPMI640 media containing 50 IU/ml IL-2 and 5% autologous plasma was used, and the cell mixture was cultured to have a final concentration of 2×107 cells/10 ml/flask.

Figure 6:
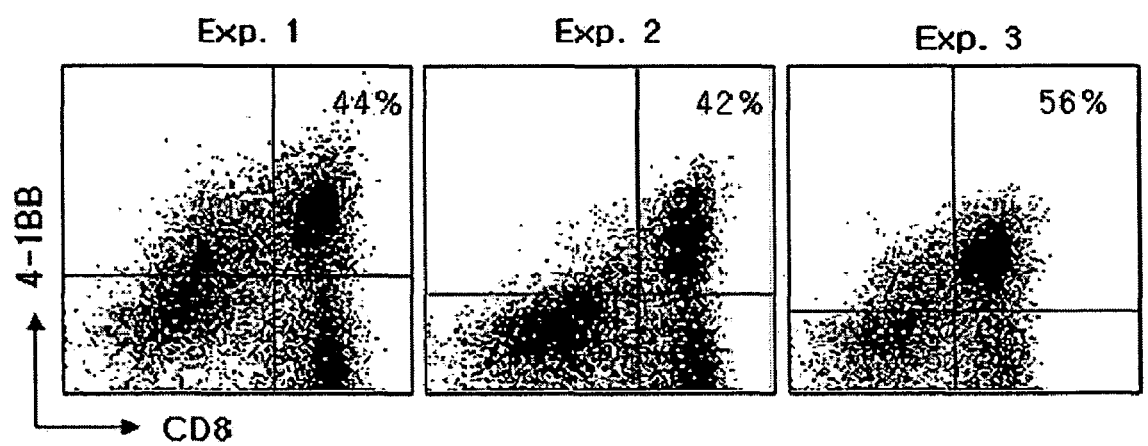
FIG. 6 illustrates increased expression of 4-1BB in CMV-specific CD8+ T cells using blast T cells labeled with CMV peptide antigens.
Figure 7:
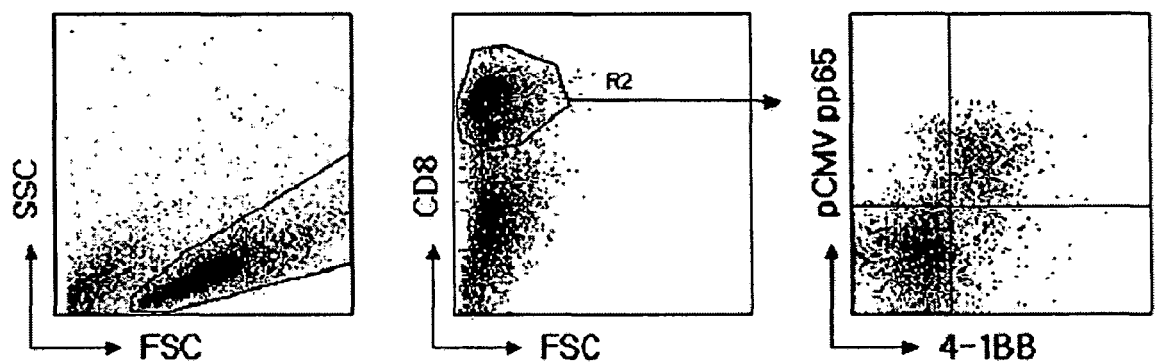
FIG. 7 illustrates compatibility between 4-1BB+ CD8+ T cells and pCMV pp65+ CD8+ T cells.

12-well culture plate (Nunclone, Cat# 150628)
2) The cells were cultured in a CO2-humidified incubator for 48 hours at 37° C.
3) After two days of the cell culture, the population of 4-1BB+ CD8+ T cells was analyzed using PE-conjugated anti-4-1BB antibodies on a flow cytometer.
   PE-conjugated anti-4-1BB mAb; BD Pharmingen
   FITC-conjugated-CD8 mAB; BD Pharmingen Labeled blast T cells were mixed with CD8+ T cells activated by peptides in a range of ratios of 1:1 up to 1:10, and the cells were cultured for two days to induce reactivation of antigen-specific CD8+ T cells. In result, as illustrated in FIG. 6, 4-1BB expression increased in the CD8+ T cells cultured with the peptide-labeled blast T cells. In most experiments, the 4-1BB expression was found in about 35 to 60% of the CD8+ T cells, and 4-1BB expression in pCMV pp65 pentamer+ CD8+ T cells was compared with that in the reactivated cells by triple-staining the cells with 4-1BB, pCMV pp65 pentamers and CD8 antibodies. In result, as illustrated in FIG. 7, 4-1BB expression was found in almost every pCMV pp65 pentamer+ CD8+ T cells. Consequently, it can be proven that the 4-1BB-expressed cells are the same as the pCMV pp65 pentamer+CD8+ T cells.

1-4. Isolation and Proliferation of 4-1BB+ CD8+ T Cells

For isolation of 4-1BB+ CD8+ T cells increased in number using antigen-labeled blast T cells, a panning method using an anti-4-1BB antibody was used.

1) 10 ml of anti-4-1BB (4B4 or 75G1) antibodies diluted in PBS at a concentration of 10 μg/ml was added to a flask, and the flask was kept for 20 to 24 hours at 4° C.
2) The supernatant containing the antibodies was removed, 10 ml of 2.5% BSA solution in PBS was added to the cells without washing, and then the cells were kept for 20 to 24 hours at 4° C.
3) The BSA solution was removed, and the cells were washed with 15 ml of PBS twice.
4) The cells prepared according to experimental example 1-3 were resuspended in X-VIVO 10 media, and the cell suspension was contained in a humanized anti-4-1BB antibody-coated flask, and then cultured in a CO2-humidified incubator for an hour at 37° C.
5) After the cell culture, the supernatant was removed and the cells were washed with 10 ml of RPMI 160 media to remove non-specific bindings.
6) X-VIVO 10 media containing 1% of autologous plasma and 1000 IU/ml of IL-2 was added to the cells in a separate flask, and then the cells were cultured for 14 days.

First, to measure purity and phenotypes of isolated cells, after one day of the cell culture, some of the cells were taken and stained. The cells were isolated by panning pCMV pp65+ CD8+ T cells reactivated by CMV peptide-labeled blast T cells for two days using anti-4-1BB antibodies. The isolated cells were cultured in media containing 1000 IU/ml human IL-2, and one day later, some of them were taken and stained with anti-CD8-PE-Cy5, pCMV pp65-PE, and anti-CD27–, anti-CD62L– or anti-NKG2D-FITC antibodies. The relative population of pCMV pp65+ CD8+ T cells to all isolated cells was measured by flow cytometry analysis, and an expression level of pCMV to CD27, CD62L or NKG2D was measured by gating the CD8+ T cells.

As illustrated in FIG. 8, the analysis results show that the percentage population of pCMV+ CD8+ T cells among the isolated cells is 60 to 80%. It may be noted that the isolated cells have a phenotype of CD27–CD62L–NKG2D+, and when the CD8+ T cells are activated, the expressions of CD27 and CD62L deteriorate, whereas, the expression of NKG2D is enhanced. Thus, it can be confirmed that the finally isolated cells are typical effector/memory CD8+ T cells.

Experimental Example 2

Comparison with Conventional Method of Isolating Antigen-Specific CD8+ T Cells using Pentamer Conventionally, a method of isolating antigen-specific CD8+ T cells using a tetramer or pentamer has been used (Luxembourg A T et al., Biomagnetic isolation of antigen-specific CD8+ T cells usable in immunotherapy, Nat. biotechnol., 16, pp. 281-285, 1998). To determine which is the superior method between a panning method using an anti-4-1BB antibody according to the present invention and the conventional method using a pentamer, a recovery rate of antigen-specific cells by the panning method using anti-4-1BB was compared with that by the conventional method using a pentamer.

According to the method described in experimental example 1-4, pCMV pp65+CD8+ T cells were isolated using anti-4-1BB antibodies, whereas, according to the conventional method using pentamers, pCMV pp65+ CD8+ T cells were isolated using pCMV pp65 pentamers and anti-PE-microbeads (Miltenyi Biotec). By comparing the number of pCMV pp65+ CD8+ T cells before panning using the anti-4-1BB antibodies with the number of the finally isolated pCMV pp65+ CD8+ T cells, a recovery rate was determined, as illustrated in FIG. 9A. The cells isolated in both methods described above were plated on separate 24-well plates at a confluency of 1×106 cells/well, cultured for 7 days with 1000 IU/ml human IL-2, and then counted to estimate proliferation rates (fold), illustrated in FIG. 9B. Recovery rates of antigen-specific CD8+ T cells isolated using humanized anti-4-1BB antibodies (SEQ. ID. Nos. 2, 3, 5 and 6: HBBK4-75G1, HBBK4-75G4, HBBK4-94G1 and HBBK4-94G4) are illustrated in FIG. 9C.

Referring to FIG. 9A, it can be noted that when CMV-specific CD8+ T cells were isolated using pentamers and anti-R-phycoerythrin (PE)-microbeads, recovery rates were 30 to 55%, whereas, when using anti-4-1BB antibodies, recovery rates were 50 to 75%. Further, it can be noted that when the cells isolated by the separate methods were cultured for 7 days under the conditions described in experimental example 1-4, CD8+ T cells isolated using anti-4-1BB antibodies increased in number faster (see FIG. 9B). Antigen-specific CD8+ T cells were isolated using humanized anti-4-1BB antibodies (SEQ. ID. Nos. 2 to 7) developed based on antigen-4-1BB antibodies (4B4) derived from a rat to measure recovery rates. Contrary to expectations, as illustrated in FIG. 9C, humanized antigens (e.g., SEQ. ID. No. 2: HBBK4-75G1 and SEQ. ID. No. 5: HBBK4-94G1) fused with human IgG1 Fc exhibited higher recovery rates than anti-4-1BB antigens (4B4) derived from a rat.

From the above results, it can be concluded that the method of isolating antigen-specific CD8+ T cells using anti-4-1BB antibodies is more efficient than the conventional isolation method using either tetramers or pentamers, and the cells isolated by the former method exhibit higher viability and proliferation rate than those isolated by the conventional method. Particularly, it can be understood that when cells have to be isolated using tetramers or pentamers, which have low affinity, in the presence of EBV illustrated in FIG. 1B, a cell recovery rate decreases. However, since 4-1BB is expressed in activated CD8+ T cells at a constant level, the isolation method using 4-1BB does not have this disadvantage (Kim Y H et al., 4-1BB costimulation enhances HSV-1-specific CD8+ T cell responses by the induction of CD11c+ CD8+ T cells, Cell Immunol., 238, pp. 76-86, 2005; Wilcox R A et al., Provision of antigen and CD137 signaling breaks immunological ignorance, promoting regression of poorly immunogenic tumors, J. Clin. Invest, 109, pp. 651-659, 2002). Moreover, it can be understood that the high viability and proliferation rate of CD8+ T cells isolated using anti-4-1BB antibodies are caused by inhibition of AICD due to a 4-1 BB stimulus in cell isolation. And, it can be confirmed that antigen-specific CD8+ T cells isolated using humanized anti-4-1BB antibodies exhibit excellent recovery rates.

Experimental Example 3

Figure 10A:
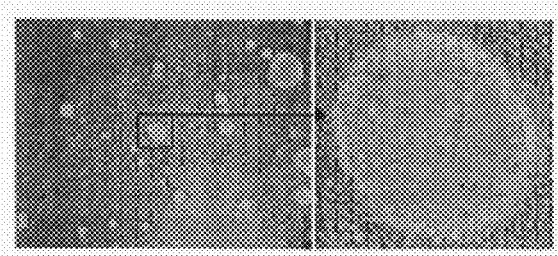
FIG. 10A is a photograph (×10) of proliferating cells, which form colonies of CD8+ T cells, on the $7^{th}$ day of cell culture.
Figure 10B:
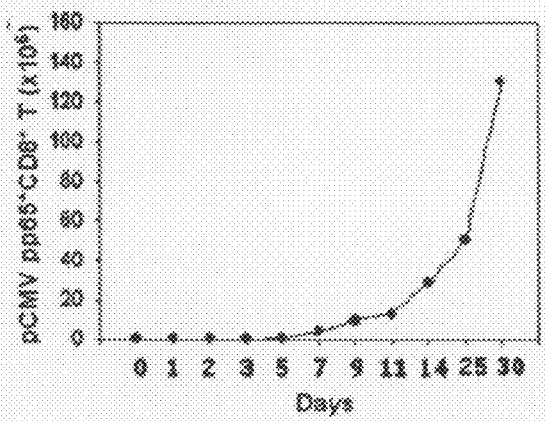
FIG. 10B is a graph illustrating a proliferation rate of CMV pp65-specific CD8+ T cells after the cell culture.

Mass-Production of Antigen (CMV pp65)-Specific CD8+ T Cells 4-1BB+ CD8+ T cells were isolated using anti-4-1BB antibodies, and CMV pp65-specific CD8+ T cells isolated according to the method described in experimental example 1-4 were proliferated using 1000 IU/ml of human IL-2. FIG. 10A is a photograph (×10) of proliferating cells, which form colonies of CD8+ T cells, on the $7^{th}$ day of cell culture. FIG. 10B is a graph illustrating a proliferation rate of CMV pp65-specific CD8+ T cells after the cell culture. Some of the cells were taken at separate dates indicated in the drawing, and stained with pCMV pp65-PE and anti-CD8-FITC for flow cytometry analysis. By counting all of the cells, the number of the pCMV pp65+ CD8+ T cells was measured. Approximately 5 to $10 \times 10^7$ PBMCs were contained in 50 ml of blood, of which 0.2 to 0.5% of CMV pp65-specific CD8+ T cells were present. Consequently, $5 \times 10^5$ or less CMV pp65-specific CD8+ T cells were present in the 50 ml of blood, and in most cases, 1 to 3×10 cells were present. As illustrated in FIG. 10B, the number of proliferating CMV pp65-specific CD8+ T cells in 50 ml of blood was at least $10^8$ cells on the $30^{th}$ day of the cell culture. That is, by the method according to the present invention, the number of antigen-specific CD8+ T cells may increase by 500 to 1500 times.

Experimental Example 4

Flow Cytometry Analysis

Figure 11:
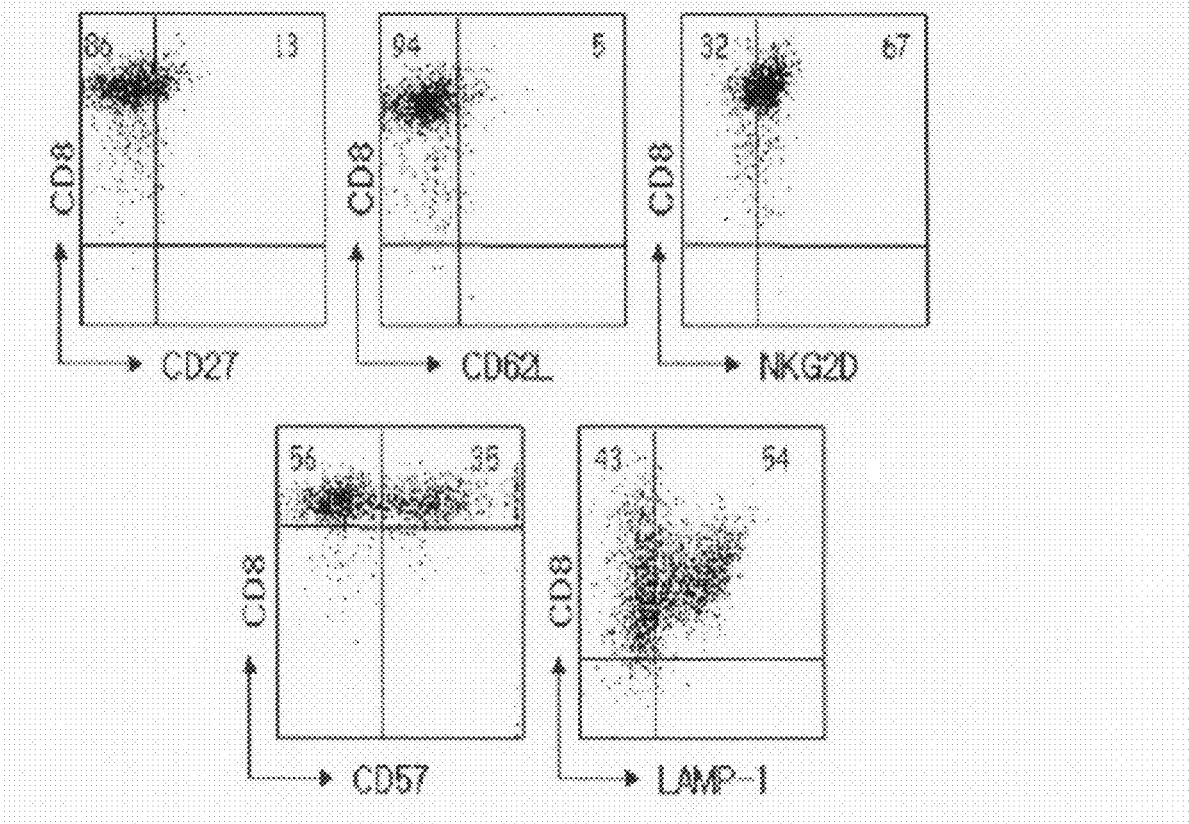
FIG. 11 illustrates phenotypes of finally produced CD8+ T cells.

By phenotype analysis of the mass-produced CMV-specific CD8+ T (CTL), a degree of aging, a function and an activation stage were detected. The CMV pp65+CD8+ T cells isolated by a panning method using anti-4-1BB antibodies were cultured with 1000 IU/ml human IL-2. On the 14th day of the cell culture, cells were taken and stained with pCMV pp65-PE, anti-CD8-PE-Cy5 and anti-CD27–, anti-CD62L–, anti-NKG2D- or anti-CD57-FITC. Expressions of CD8 to CD27, CD62L, NKG2D and CD57 were measured by gating only pCMV pp65+ T cells. To analyze expression of LAMP-1, the cultured cells were plated on separate 95-well plates and then cultured for 5 hours with CMV peptides, monensin, and anti-LAMP-1 (CD107a)-biotin antibodies. After that, the cells were stained with streptavidin-PE and anti-CD8-FITC to determine a population of LAMP-1+ CD8+ T cells, which is illustrated in FIG. 11. An analysis method employed here is as follows.

In order to prevent non-specific binding of pigment antibodies with Fc parts, the cells were treated with 10 μl of 1 mg/ml human IgG solution for 10 minutes at 4° C. Then, the cells were stained with surface molecule-specific antibodies for 30 minutes at 4° C. The cells stained with the antibodies were washed with PBS containing 0.1% BSA twice, and then phenotypes of the surface molecules in the separate samples were analyzed on a flow cytometer (BD Bioscience, San Diego, Calif.).

The analysis results show that the pCMV pp65+ CD8+ T cells are CD27-CD62L-NKG2D+ T cells, which are typical effector/memory CD8+ T cells. Only approximately 25 to 35% of the cells exhibited positive responses to CD57 that was used as an aging indicator. To measure an effector function (cytotoxicity), cellular surface expression of LAMP-1 was analyzed, and therefrom it can be noted that only 40 to 60% of the cells had an effector function. Consequently, the finally differentiated CD8+ T cells included finally differentiated CD8+ T cells having an effector function, and proliferating and differentiating cells.

Experimental Example 5

CD107 Mobilization Assay

To investigate antigen-specific CTC function, a degree of exposure of a cell surface was measured. Cells were plated on a 96-well plate at a confluency of $2 \times 10^6$ cells/well, and then treated with 5 μg/ml of CMV peptides. At the same time, 1 μl of 2 mM monensin (Sigma) and anti-CD107a-biotin antibodies were added to a separate well. The cells were mixed by a multichannel pipette, and the plate was centrifuged into a pellet at 300×g for one minute. Then, the cells were cultured for 5 hours at 37° C. The cultured cells were harvested from the separate wells and washed with PBS containing 0.02% azide and 0.5 mM of EDTA to break bindings between cells. The cells were stained with streptavidin-FITC, anti-CD8-PE-Cy5 and pentamer-PE for 30 minutes, and then analyzed on a flow cytometer.

As described above, methods of isolating and proliferating antigen-specific CD8+ T cells using anti-4-1BB antibodies may overcome the shortcoming of a low recovery rate due to a low affinity of tetramers or pentamers in a conventional isolation method. Further, by using humanized anti-4-1BB antibodies, antigen-specific cells can be isolated at a high recovery rate and grown at a high proliferation rate. Thus, antigen specific CD8+ T cells yielded by the isolation and proliferation methods of the present invention may be used to treat cancer without any side-effects.

Exemplary embodiments of the present invention have been disclosed herein and, although specific terms are employed, they are to be interpreted in a generic and descriptive sense only, not for the purpose of limitation. Accordingly, it will be understood by those of ordinary skill in the art that various changes in form and details may be made without departing from the spirit and scope of the present invention as set forth in the following claims.

What is claimed is:

1. A method of isolating CMV peptide-specific CD8+ T cells using anti-4-1BB antibodies, said method comprising the steps of:
   1) isolating peripheral blood mononuclear cells (PMBCs) from blood and culturing the cells in culture media with CMV peptide;
   2) isolating PMBCs from the same blood as in the previous step, culturing the cells with OKT3 antibody, and washing and labeling the cells with CMV peptide;
   3) culturing a cell mixture consisting of the cultured cells in step 1) and the labeled cultured cells in step 2) in a range of ratios from 1:1 to 10:1 for 1 to 3 days;
   4) culturing the cell mixture in step 3) in an anti-4-1BB mAb coated culture plate and removing unattached or non-specifically bound cells; and
   5) culturing attached cells in step 4) and harvesting all of the cells.

2. The method according to claim 1, wherein the media in step 1) contains autologous plasma or autologous serum.

3. The method according to claim 1, wherein, in step 1), the cells are cultured for 12 to 16 days.

4. The method according to claim 1, wherein conditions of media and culture time in step 2) are the same as in step 1).

5. The method according to claim 1, wherein the cells in step 3) are cultured in a media containing IL-2 and autologous plasma.

6. The method according to claim 1, wherein, in step 4), the cells are cultured for 1 to 3 hours.

7. A method of isolating CMV peptide-specific CD8+ T cells using humanized anti-4-1BB antibodies, said method comprising the steps of:
   1) isolating peripheral blood mononuclear cells (PMBCs) from blood and culturing the cells in culture media with CMV peptide;
   2) isolating PMBCs from the same blood as in the previous step, culturing the cells with OKT3 antibody, and washing and labeling the cells with CMV peptide;
   3) culturing a cell mixture consisting of the cultured cells in step 1) and the labeled cultured cells in step 2) in a range of ratios from 1:1 to 10:1 for 1 to 3 days;
   4) culturing the cell mixture in step 3) in an humanized anti-4-1BB antibody of SEQ ID No. 6 coated culture plate and removing unattached or non-specifically bound cells; and
   5) culturing attached cells in step 4) and harvesting all of the cells.

8. A method of proliferating CMV peptide-specific CD8+ T cells, comprising isolating the cells according to the method of claim 1, and culturing the isolated cells in culture media.

9. The method according to claim 8, wherein the cells are cultured in media containing autologous plasma and IL-2.

10. The method according to claim 8, wherein the cells are cultured for 12 to 16 days.

11. A method of proliferating CMV peptide-specific CD8+ T cells, comprising isolating the cells according to the method of claim 7, and culturing the isolated cells in culture media.

12. The method according to claim 11, wherein the cells are cultured in media containing autologous plasma and IL-2.

13. The method according to claim 11, wherein the cells are cultured for 12 to 16 days.

* * * * *